(12) United States Patent
von Pechmann et al.

(10) Patent No.: US 8,460,171 B2
(45) Date of Patent: Jun. 11, 2013

(54) ENDOSCOPIC MESH DELIVERY SYSTEM WITH INTEGRAL MESH STABILIZER AND VAGINAL PROBE

(76) Inventors: Walter von Pechmann, Bethesda, MD (US); Samuel C Yoon, Clarksville, MD (US); Keith Lipford, Baltimore, MD (US); Brian Lipford, Bel Air, MD (US); Austin Cox, Baltimore, MD (US)

( * ) Notice: Subject to any disclaimer, the term of this patent is extended or adjusted under 35 U.S.C. 154(b) by 395 days.

(21) Appl. No.: 12/746,658

(22) PCT Filed: Dec. 12, 2008

(86) PCT No.: PCT/US2008/013661
§ 371 (c)(1),
(2), (4) Date: Jun. 7, 2010

(87) PCT Pub. No.: WO2009/078953
PCT Pub. Date: Jun. 25, 2009

(65) Prior Publication Data
US 2010/0280309 A1 Nov. 4, 2010

Related U.S. Application Data

(60) Provisional application No. 61/005,746, filed on Dec. 7, 2007.

(51) Int. Cl.
*A61F 2/00* (2006.01)
*A61F 13/00* (2006.01)

(52) U.S. Cl.
USPC .......................................................... 600/37

(58) Field of Classification Search
USPC ............. 600/9, 11, 29, 30, 37, 591, 459, 462; 606/139, 151; 623/23.72; 128/885, 897; 604/19, 604/47, 164.08, 192
See application file for complete search history.

(56) References Cited

U.S. PATENT DOCUMENTS

| | | | |
|---|---|---|---|
| 5,810,806 A * | 9/1998 | Ritchart et al. | 606/45 |
| 6,080,118 A * | 6/2000 | Blythe | 600/591 |
| 6,328,729 B1 | 12/2001 | Jervis | |
| 6,348,036 B1 * | 2/2002 | Looney et al. | 600/232 |
| 6,497,706 B1 * | 12/2002 | Burbank et al. | 606/45 |
| 6,741,895 B1 * | 5/2004 | Gafni et al. | 607/138 |
| 6,932,759 B2 | 8/2005 | Kammerer et al. | |
| 7,052,453 B2 | 5/2006 | Presthus et al. | |

(Continued)

OTHER PUBLICATIONS

Culligan et al., Long-Term Success of Abdominal Sacral Colpopexy Using Synthetic Mesh, Am. J. Obstet. Gynecol., Dec. 2002.

*Primary Examiner* — Charles A Marmor, II
*Assistant Examiner* — Eileen Foley
(74) *Attorney, Agent, or Firm* — Ober, Kaler, Grimes & Shriver; Royal W. Craig

(57) ABSTRACT

A mesh delivery system (2) for sacral colpopexy procedures is disclosed. The system (2) uses a mesh stabilizer (30), an endoscopic introducer (2) that carries the mesh stabilizer (30) into the abdomen, and a vaginal probe (10) (inserted through the vagina) with a head that interfaces with the mesh stabilizer (30) in lock-and-key fashion. The mesh stabilizer (30) delivers mesh straps for sacral colpopexy into the abdomen. After delivery, the stabilizer (30) interfaces with the probe (10) head and locks the mesh stabilizer (30) with mesh straps in place. The endoscopic introducer (20) can then be temporarily detached and removed to facilitate suturing of the mesh to the anterior and posterior vaginal walls. After permanent suturing, the introducer (20) can be reinserted and used to retrieve the mesh stabilizer (30) component.

17 Claims, 8 Drawing Sheets

U.S. PATENT DOCUMENTS

| | | | |
|---|---|---|---|
| 7,942,806 B2 * | 5/2011 | Tracey et al. | 600/29 |
| 8,109,867 B2 * | 2/2012 | Rosenblatt | 600/37 |
| 2003/0195386 A1 | 10/2003 | Thierfeld et al. | |
| 2003/0220538 A1 * | 11/2003 | Jacquetin | 600/37 |
| 2004/0230092 A1 * | 11/2004 | Thierfelder et al. | 600/37 |
| 2005/0065395 A1 | 3/2005 | Mellier | |
| 2006/0015001 A1 | 1/2006 | Staskin et al. | |
| 2006/0199994 A1 | 9/2006 | Inman et al. | |
| 2007/0129615 A1 | 6/2007 | Backman et al. | |
| 2007/0161849 A1 * | 7/2007 | Goldberg | 600/30 |
| 2009/0187235 A1 * | 7/2009 | Kaplan et al. | 607/89 |

* cited by examiner

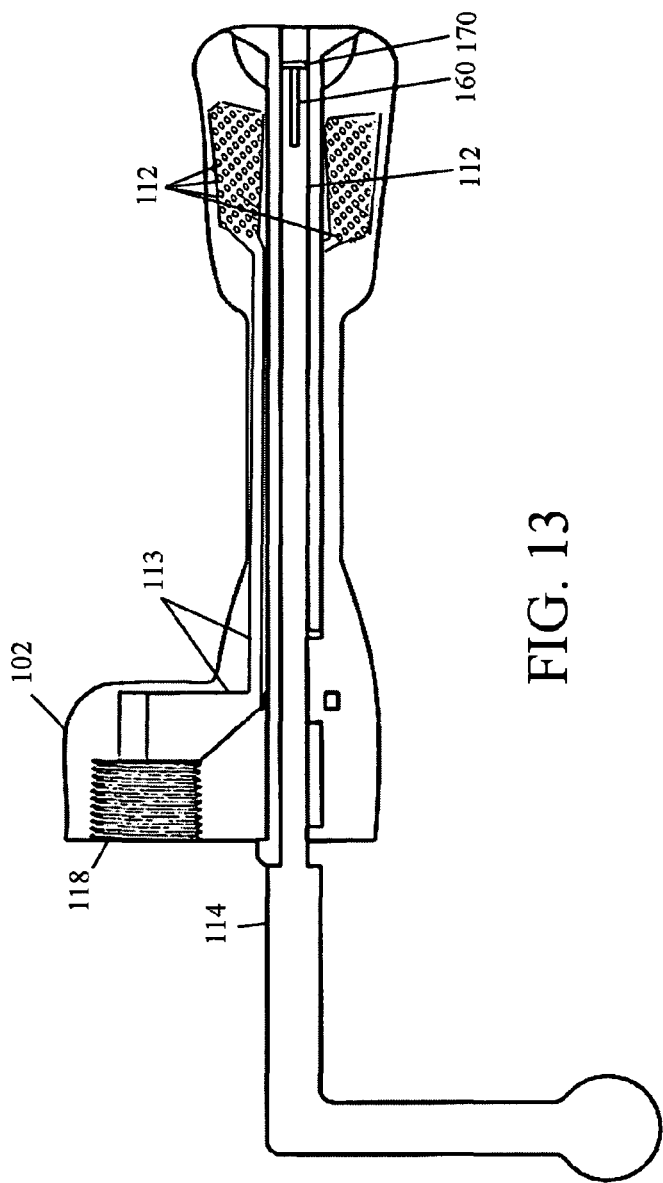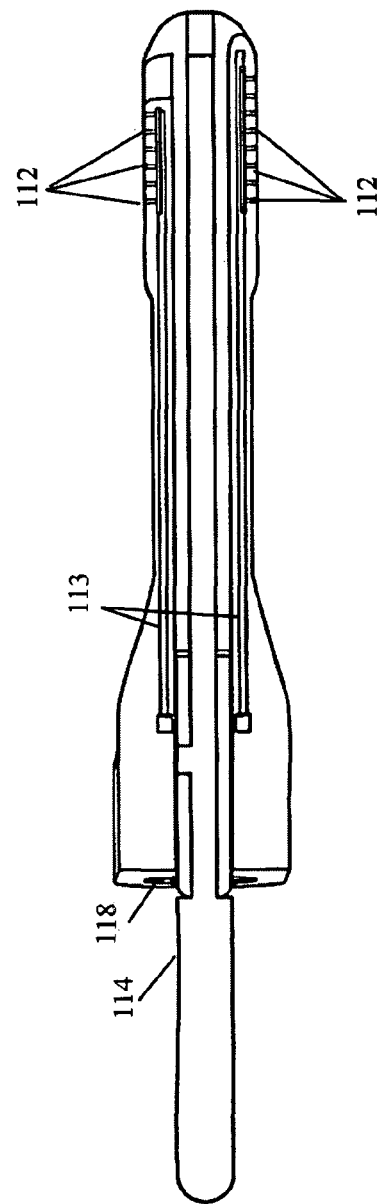
FIG. 13
FIG. 14

ENDOSCOPIC MESH DELIVERY SYSTEM WITH INTEGRAL MESH STABILIZER AND VAGINAL PROBE

CROSS-REFERENCE TO RELATED APPLICATIONS

This application is a National Stage of International Application No. PCT/US2008/013661, filed on Dec. 12, 2008 and claims priority from U.S. Provisional Application 61/005,746 filed on Dec. 7, 2007.

BACKGROUND OF THE INVENTION

1. Technical Field

The present invention relates to medical methods and devices for performing sacral colpopexy.

2. Background Art

The sacral colpopexy operation is designed to recreate support to the upper vagina by attaching straps of permanent synthetic mesh to the upper anterior and posterior vaginal walls and then suspending the other end of the straps on the anterior surface of the sacrum. This operation is one of many operations described for the correction of pelvic organ prolapse but is considered the gold standard for correction of prolapse of the upper vagina. See, for example, "Long-Term Success Of Abdominal Sacral Colpopexy Using Synthetic Mesh", Culligan et al. Am J Obstet Gynecol (December 2002). This operation can be done either for correction of vaginal vault prolapse in patients who have previously undergone hysterectomy or can be done at the time of hysterectomy in patients with uterine prolapse. In the latter case, many physicians prefer to perform supracervical hysterectomy because of data suggesting that mesh related complications are less likely in cases of supracervical compared with total hysterectomy.

The sacral colpopexy operation was first described as being done through a large incision in the abdominal wall (laparotomy) and is still predominantly done in that manner.

FIG. 1 is a diagrammatic illustration of the surgery, which is usually performed under general anesthesia. An incision is made in the lower abdomen. The bladder and rectum are freed from the vagina and permanent mesh is secured to the sacrum (upper tailbone) to support the front and back wall of the vagina. The mesh is sutured to the vagina. The peritoneum (lining of the abdominal cavity) is closed over the mesh. There is growing interest in performing this operation via less invasive approaches, such as laparoscopy or robot-assisted laparoscopic surgery, but existing vaginal probes, surgical instruments and mesh configurations are not well-suited for this.

There are a variety of vaginal probes and mesh configurations designed for use in treating disorders of the female pelvic floor such as pelvic organ prolapse, urinary incontinence, and sexual dysfunction.

For example, U.S. Pat. No. 6,741,895 to Gafni et al. (Medoc Ltd.) issued May 25, 2004 shows a vaginal probe and method for stimulation of the nerves of the vagina with the purpose of testing their reaction to stimuli in the hope of defining, and treating sexual dysfunction in women. A balloon structure is used to provide tactile stimuli. When the balloon is inflated, these projections poke into the vagina.

United States Patent Application 20060199994 by Inman et al. (AMS Research) issued Sep. 7, 2006 shows surgical instruments useful in pelvic floor repair procedures. The claims require a handle attached to a slender, metal, curved rod.

United States Patent Application 20030220538 to Jacquetin issued 27 Nov. 2003 discloses a particular mesh implant for treating anterior vaginal prolapse.

U.S. Pat. No. 6,932,759 to Kammerer et al. issued Aug. 23, 2005 shows a surgical instrument and method for treating female urinary incontinence with a curved needle-like element and a proximal tape, or mesh, for implanting into the lower abdomen of a female to provide support to the urethra. A second curved needle element is used for simultaneous attachment to the distal end of the first needle.

The IVS Tunneller™ device is available from U.S. Surgical of Norwalk, Conn. The IVS device comprises a fixed delta wing handle, a hollow metal tube and a stylet that is placeable within the tube. The stylet has a rounded plastic tip on one end and an eyelet at the other end. The device may be used to implant a polypropylene tape for infracoccygeal sacropexy and other surgical procedures.

Although the foregoing references have some relevance, they are not suitable for sacral colpopexy, and would not be useful in this latter context. U.S. Pat. No. 6,328,729 (General Surgical Innovations) to Jervis issued Dec. 11, 2001 shows a colporrhaphy method and apparatus in which a tunneling member is advanced and a balloon inflated, thereby dissecting the anatomical space. Again, this device is designed to facilitate dissection of anatomical spaces and is not useful for sacral colpopexy.

United States Patent Application 20060015001 to Staskin et al. (American Medical) issued Jan. 19, 2006 shows a sling delivery system to treat urological disorders. The U-shaped configuration of the sling assembly also allows the sling to be adjusted during and/or after implantation. This device is designed for treatment of incontinence and neither it nor any of the foregoing devices are suitable for performance of sacral colpopexy.

United States Patent Application 20030195386 to Thierfelder et al. (AMS Research Corporation) issued Oct. 16, 2003 shows a surgical kit useful for performing a surgical procedure such as a sacral colpopexy with an implantable Y-shaped suspension for treating pelvic floor disorders such as vaginal vault prolapse. AMS also has a device called the Straight-In™ System which uses a long slender instrument designed for endoscopic use that screws a small coil of wire through the pre-formed Y-graft mesh and into the sacrum, thereby obviating the need to suture the mesh to the anterior longitudinal ligament of the sacrum. This device and the mesh are fairly described in the '386 patent application. Unlike the above-described references, this mesh configuration is created specifically for sacral colpopexy. However, there is no described means of stabilizing the mesh in the desired position during suturing of the mesh to the vagina.

There has recently been a growing interest in performing the sacral colpopexy operation via less invasive approaches, such as laparoscopy or robot-assisted laparoscopic surgery. Sacral colpopexy has been performed laparoscopically through multiple ports, in one case three to four ports for a daVinci® robot, and one or two ports for the assistant. The polypropylene mesh was attached robotically to the sacral promontory and to the vaginal apex using Gortex™ sutures. Whether performed manually or robotically, there are still inherent problems with manipulating the end effectors and stabilizing the vagina.

Performing the operation laparoscopically using currently available equipment has several inefficiencies. One of the problematic areas in performing laparoscopic or robotic sacral colpopexy is introduction and positioning of the mesh straps during suturing of the mesh to the vagina. Guiding them into proper orientation is awkward. Maintaining them in the proper position during suturing requires constant vigilance on the part of the assistant as they frequently require repositioning. Additionally, maintaining the mesh straps in position occupies one or more instruments that could be utilized elsewhere (for instance in retracting the surrounding tissues for better visualization). Sometimes portions of the mesh will drape over and obscure the site of interest, particularly during suturing the posterior strap of mesh to the posterior vaginal wall.

It has been proposed in other contexts to stabilize one surgical instrument using a second instrument inserted through another incision. For example, U.S. Pat. No. 7,052,453 to Presthus et al. (Solorant Medical) issued May 30, 2006 shows an incontinence treatment with urethral guide that docks with a probe. Generally, the guide can be inserted into a first body orifice and the probe can be inserted into a second body orifice and placed in a predetermined position relative to the guide so as to position the treatment surface adjacent the target tissue in the second body orifice. The urethral guide and probe may align RF sensors relative to a tissue surface.

It would be greatly advantageous to provide a mesh delivery system that overcomes the alignment and positioning problems using a docking concept as above, rendering the mesh attachment for sacral colpopexy more efficient. If the operation can be rendered more efficient, i.e., less time consuming, and with a lower learning curve, there is potential for the operation to be transformed in to one that is done primarily laparoscopically, similar to what has already occurred with cholecystectomy (removal of the gall bladder).

DISCLOSURE OF INVENTION

It is an object of the present invention to provide a mesh delivery system for sacral colpopexy that facilitates attachment of supporting (anterior and posterior) mesh straps.

It is another object to provide a mesh delivery system for sacral colpopexy that includes an endoscopic mesh introducer that docks with a stabilized vaginal probe to stabilize the inserted mesh for suturing.

It is another object to stabilize the vagina in a fixed but adjustable position during dissection of the tissue planes necessary to allow safe attachment of mesh to the vagina without causing injury to the rectum or bladder.

It is another object to stabilize the vagina in a fixed but adjustable position during suturing of mesh to the vagina.

Other objects, features, and advantages of the present invention will become more apparent from the following detailed description of the preferred embodiments and certain modifications thereof in which a mesh delivery system is provided for sacral colpopexy. The system generally comprises a mesh stabilizer, an endoscopic introducer that carries the mesh stabilizer into the abdomen, and a vaginal probe with a head that interfaces with the mesh stabilizer to dock therewith in a lock-and key manner. The probe may be handheld, robotically-held, or adjustably anchored via a supporting framework to a support surface such as the operating table. The vaginally placed probe essentially acts as a stabilizer for the vaginal tissue during dissection of the bladder and rectum away from the vagina and then during suturing of mesh to the vagina. The system is designed to deliver mesh strap(s) for sacral colpopexy through a standard laparoscopic port. In general use the mesh stabilizer is introduced by the introducer through the laparoscopic port into the abdomen to both deliver and stabilize two anterior and posterior mesh straps. After delivery, the mesh stabilizer docks to the probe head (inserted into the vagina). This docking engagement locks the mesh stabilizer with mesh straps in place in the desired site with the muscular walls of the vagina lying between the vaginal probe and the mesh stabilizer. The endoscopic introducer is then temporarily detached and removed to facilitate suturing of the mesh to the anterior and posterior vaginal walls. After permanent suturing, the introducer is reinserted in to the abdomen and used to retrieve the mesh stabilizer component. The system greatly facilitates suturing of the sacral mesh to the vaginal walls and results in a safer, more effective procedure.

BRIEF DESCRIPTION OF DRAWINGS

Other objects, features, and advantages of the present invention will become more apparent from the following detailed description of the preferred embodiments and certain modifications thereof when taken together with the accompanying drawings in which:

FIG. 13 is a top cross section of the vaginal probe 10.

FIG. 14 is a side cross section of the vaginal probe 10.

BEST MODE FOR CARRYING OUT THE INVENTION

As described above, the present invention is a mesh delivery system for sacral colpopexy and a method of using the same designed specifically for laparoscopic delivery, and that renders attachment of supporting mesh straps less time consuming, and less prone to error.

Figure 2:
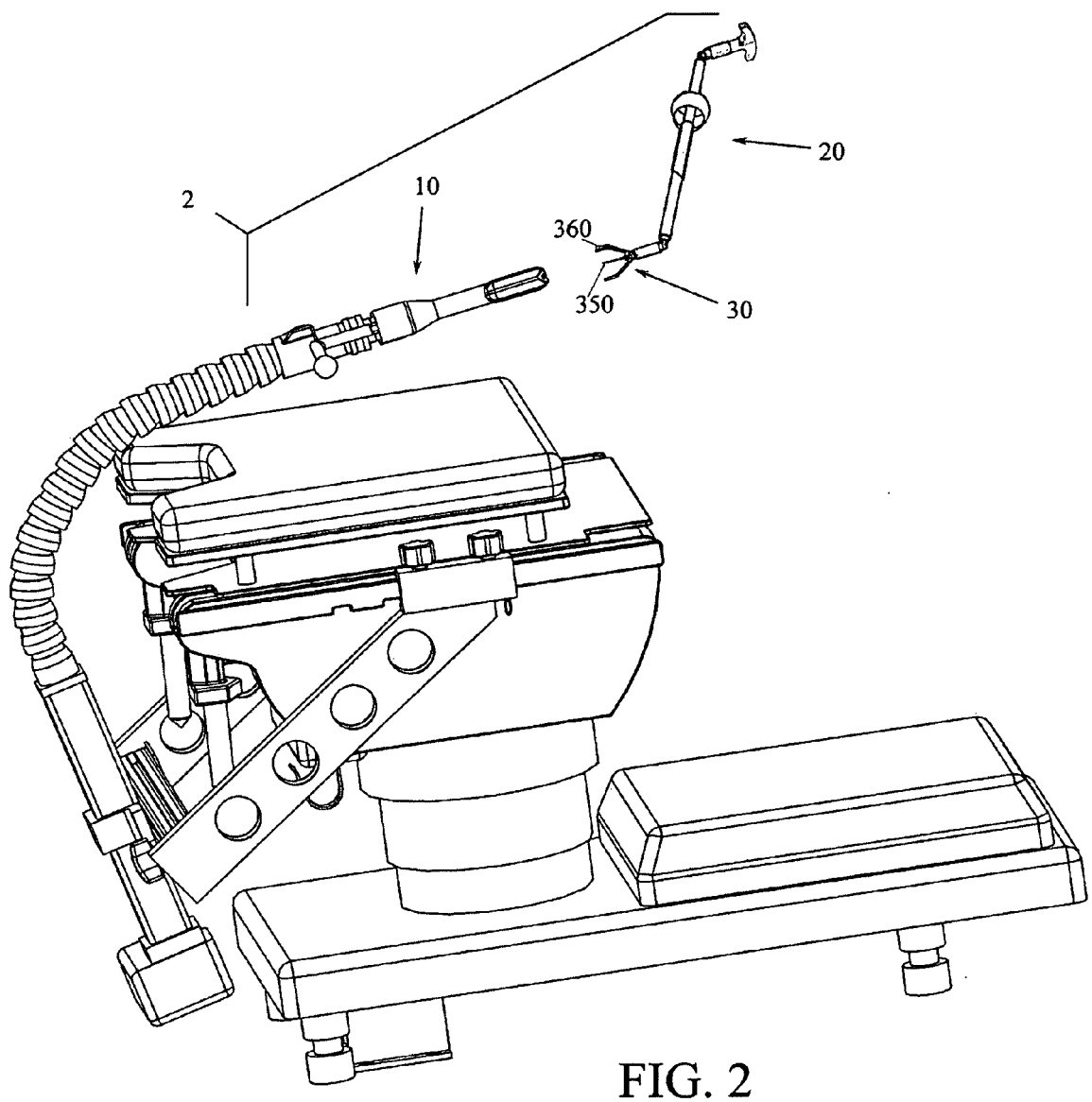
FIG. 2 is a side perspective view of a mesh delivery system 2 according to the invention atop a surgical table equipped with a stabilizer system.

FIG. 2 is a side perspective view of a mesh delivery system 2 according to the invention atop a surgical table equipped with a stabilizing arm. The mesh delivery system 2 generally comprises a vaginal probe 10 supported by a stabilizing arm (or some other stable platform), a mesh stabilizer 30 that docks with the probe 10, and an introducer 20 for endoscopically inserting the stabilizer 30 into the abdomen. In accordance with the method of use, one or more strips of sacral mesh are loaded onto the mesh stabilizer 30 (usually two strips, one anterior and one posterior). The stabilizer 30 is detachably mounted to the distal end of the introducer 20. The mesh stabilizer 30 is then introduced by the introducer 20 through a conventional trocar or laparoscopic port into the abdomen to both deliver and stabilize the mesh strips. The introducer 20 is fully articulating and helps position the mesh stabilizer 30 directly in front of the probe 10. Once in front, the mesh stabilizer 30 docks to the probe 10 in such as way as to capture the vaginal tissue against the mesh straps. While docked, the stabilizer 30 may be detached from the introducer 20, and the introducer 20 removed. The mesh straps are now fully stabilized by the docked stabilizer 30 on the probe 10, and this greatly facilitates suturing of the mesh strips to the vaginal walls. After permanent suturing of mesh straps to the vagina, the procedure is complete, and the introducer 20 may be reintroduced and used to retrieve the mesh stabilizer 30.

The present invention is suited for use with any surgical table, and all three components 10, 20 and 30 may be manually, mechanically or robotically manipulated. The illustrated surgical table is equipped with a flexible/locking stabilizing arm to which the vaginal probe 10 is distally mounted, and thereby securely holds the probe 10 during the sacral colpopexy procedure (which indeed requires a stable probe during suturing of mesh to the vagina).

Figure 3:
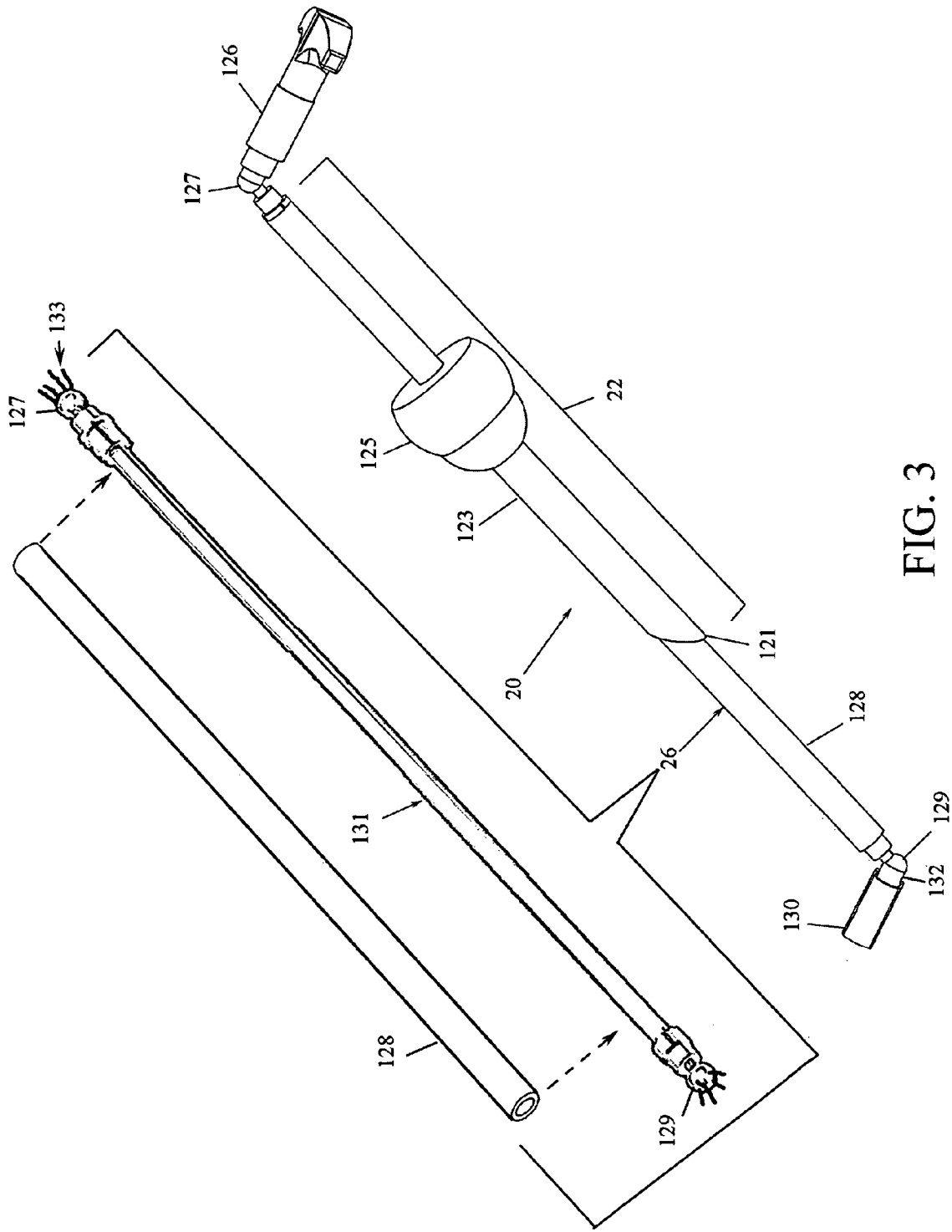
FIG. 3 is a side perspective view of the introducer 20 for inserting the stabilizer 30 into the abdomen.

FIG. 3 is a side perspective view of the introducer 20 for inserting the stabilizer 30 into the abdomen (stabilizer 30 here being contained within a holder tube 130). The introducer 20 includes a cannula 22 having a tubular member 123 formed with a sharp penetrating tip 121. A plug 125 is mounted lengthwise along the cannula 22. The cannula 22 is adapted for insertion through a trocar or port to create a defined passage into the body cavity. Plug 125 is an elastomeric member shaped for a seal against the trocar or port. The introducer 20 also includes an articulating arm 26 (exploded in inset) adapted for slidable insertion down through the tubular cannula 22. The arm 26 is of slightly smaller diameter than the tubular member 123.

A manipulator stem 126 having a handle at one end is pivotally attached at the other end to one end of the articulating arm 26, and the articulating arm 26 extends down through the cannula 22 to a holder tube 130 at the other end which houses the stabilizer 30. As seen in the inset, the articulating arm 26 further comprises a linkage assembly 131 encased within a tubular sleeve 128. The linkage assembly 131 extends to opposing ball joints 127, 129, and holder tube 130 is pivotally connected to ball joint 129 while manipulator stem 126 (with handle) is pivotally connected to the ball joint 127. Both the sleeve 128 and linkage assembly 131 pass down through the cannula 22. Motion imparted to the first ball joint 127 by the manipulator stem 126 handle is transmitted down through linkage assembly 131 to the second ball joint 129, which manipulates the holder tube 130. The handle of manipulator stem 126 may be manipulated throughout approximately a 270 degree hemispherical range of motion, and this motion is transmitted down through linkage assembly 131 to the second ball joint 129 which imparts diametrically opposite motion to the holder tube 130 attached to the second ball joint 129. Thus, for example, angular movement of manipulator stem 126 handle ten degrees upward will lower the angle of holder tube 130 by ten degrees. The linked opposed-motion operation may be implemented in a variety of ways. For example, as illustrated, at least four thin cables 133 may pass through the linkage assembly 131 and be attached (at offset points) at the base of the holder tube 130 and the base of the manipulator stem 126. This way, as the handle of manipulator stem 126 is moved by the operator, the cables 133 are actuated (pulled) in each quadrant that match the handle 126 motion. As the cables 133 move, they cause opposing motion in the holder tube 130 at the distal end of the linkage assembly 131. For example, angular movement of manipulator stem 126 handle directly upward will pull the two lower cables 133, pulling the holder tube 130 down accordingly. At least four cables 133 are preferred for suitable control over the contra-motion, although more cables may be used to increase the degree of control. One skilled in the art should understand that the core concept of the invention does not require an articulating arm 26 as described above, though the manipulation afforded thereby is presently preferred. Other embodiments may employ a non-articulating arm having similar features but lacking any articulation capability.

Figure 1:
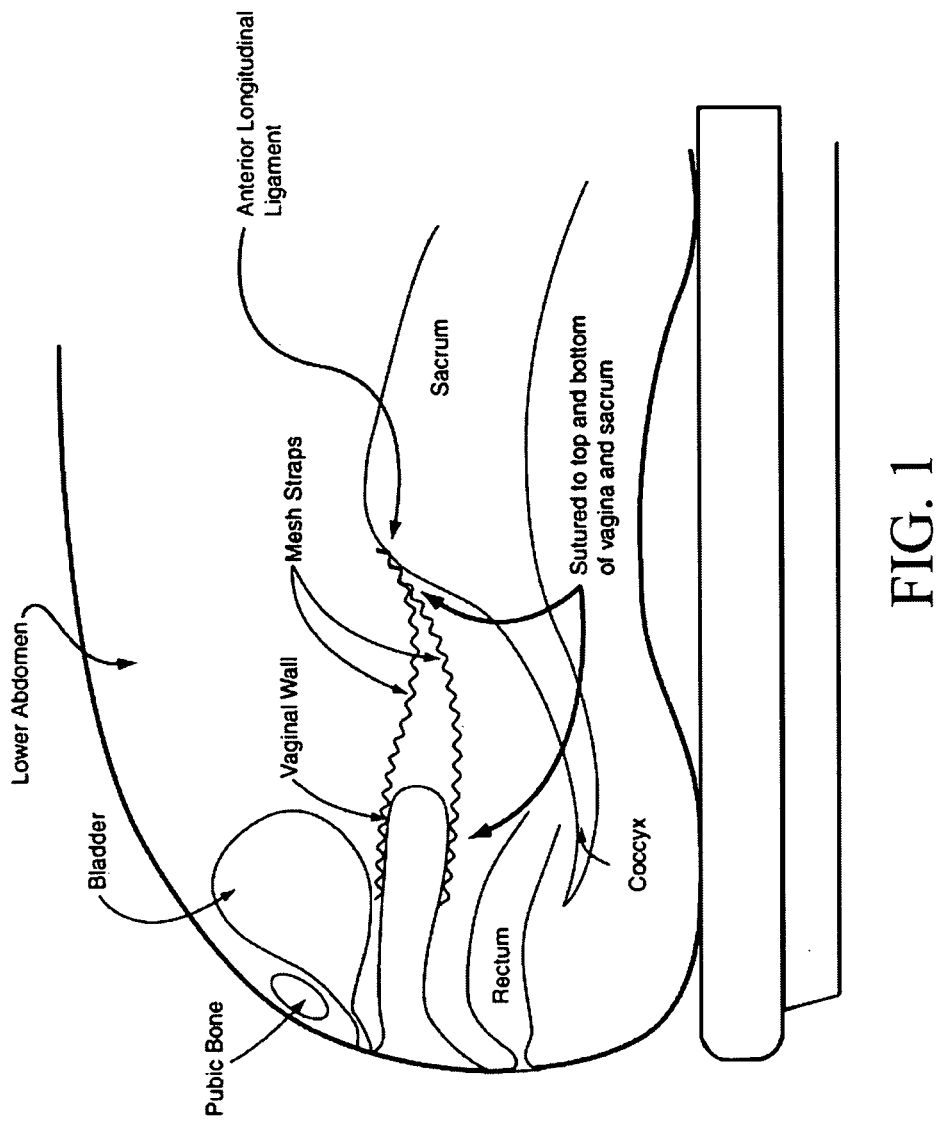
FIG. 1 is a diagrammatic illustration of a completed sacral colpopexy surgery in which straps of mesh attached to the upper vagina inferiorly are suspended on the anterior longitudinal ligament of the sacrum superiorly.

Referring back to FIG. 2, the mesh stabilizer 30 is initially contained within the holder tube 130 of the articulating arm 26, and is releasably attached therein. With the mesh stabilizer 30 inside holder tube 130, a surgeon can easily introduce the stabilizer 30 into the body cavity using the introducer 20. Once inside, the stabilizer 30 may be pushed out of the holder tube 130 as seen in FIG. 1 (this can occur automatically as the holder tube 130 and stabilizer 30 slide through the introducer 20, as the inner walls of the tubular member 123 of cannula 22 may frictionally separate the holder tube 130 from the introducer 20 In this configuration a surgeon working externally of the body cavity can manipulate the mesh stabilizer 30 throughout a full 270 degree hemispherical range of motion inside the body cavity. Once properly positioned the stabilizer 30 can be released entirely from the introducer 20.

As seen in FIG. 3, one embodiment for releasably attaching the mesh stabilizer 30 to the introducer 20 is via a small magnet or ferromagnetic material 132 insert inside the holder tube 130 at the distal end of the introducer 20. This insert 132 forms a magnetic attachment mechanism for the mesh stabilizer 30. As described below, the mesh stabilizer 30 may contains its own magnetic or ferromagnetic material insert that is attracted to the insert 132, and yet the magnetic attraction is calibrated such that when the mesh stabilizer 30 has been manipulated into position (by introducer 20) in advance of the probe 10, and is then docked thereto, removal of the introducer 20 breaks the magnetic attraction to release the stabilizer 30 to the probe 10. The introducer 20 can then be removed for unobstructed suturing. Another embodiment, which could be used alone or in conjunction with the magnet 132, is a more standard physical grabbing mechanism that is actuated by the operator at the handle 126 via additional pass-through cables or other suitable means to remotely attach and detach the mesh stabilizer 30. The details of either embodiment would be such that the operator could fully manipulate the mesh stabilizer 30, including the ability to carry torque through the attachment joint.

Figure 4:
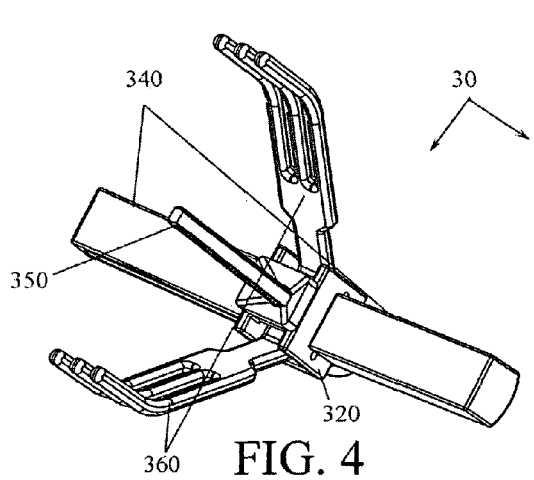
FIG. 4 is a front perspective view of the mesh stabilizer 30.
Figure 5:
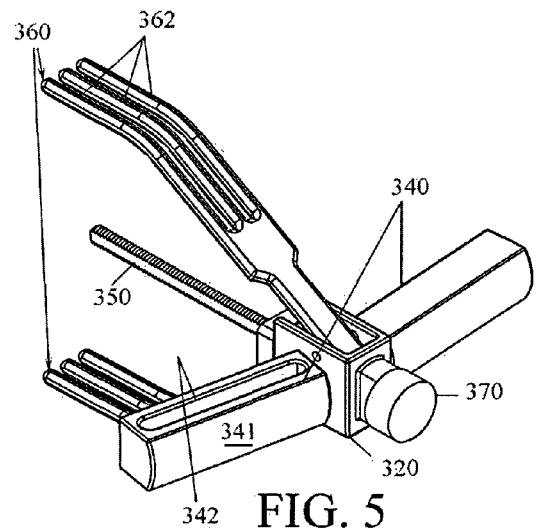
FIG. 5 is a rear perspective view of the mesh stabilizer 30.
Figure 6:
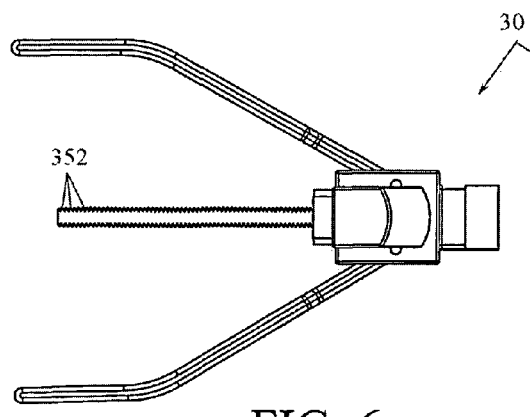
FIG. 6 is a side view of the mesh stabilizer 30.
Figure 7:
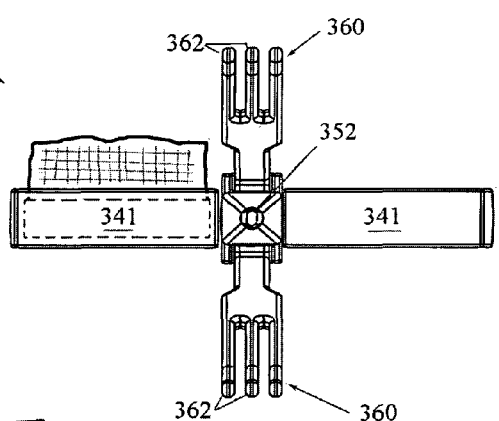
FIG. 7 is a front view of the mesh stabilizer 30.
Figure 8:
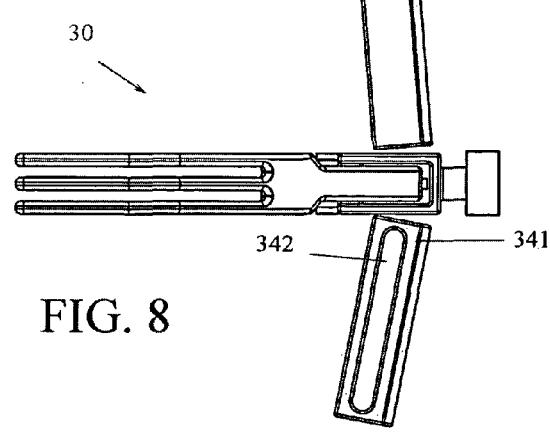
FIG. 8 is a top view of the mesh stabilizer 30.

FIG. 4 is a front perspective view, FIG. 5 is a rear perspective view, FIG. 6 is a side view, FIG. 7 is a front view, and FIG. 8 is a top view, respectively, of the mesh stabilizer 30. With collective reference to FIGS. 4-8, the mesh stabilizer 30 includes a body 320 having two opposing spring arms 360 each adapted to carry a strip of sacral mesh into contact with vaginal tissue sandwiched between the mesh stabilizer 30 and probe 10. In this regard, both spring arms 360 are foldable forks bearing a plurality of tines 362. Both spring arms 360 are pivotally mounted to the body 320 and are spring-biased outward. The spring arms 360 extend outward and branch into tines 362, which tines serve two purposes. One is to facilitate docking of the mesh stabilizer 30 with the probe 10. The open spring arms 360 guide the mesh stabilizer 30 onto the tip of probe 10. The other purpose is to carry a strip of sacral mesh, which is a conventional synthetic suspending strap such as polypropylene that will typically be woven through the tines 362. The tips of the spring arms 360 carry the mesh straps and are preferably rounded to reduce the likelihood of inadvertent penetrating injury. The tines 362 of the spring arms 360 are intended to carry the loosely woven polypropylene mesh, such that an approximately 3 cm wide by 15 cm long strap of mesh can be threaded over the three tines 362 in the distal end or preferentially over the middle tine exclusively at the distal end of the mesh to allow sliding of the lateral tines 362 over the vaginal muscularis without catching the mesh. More proximally, the mesh would be threaded at least once over all three tines 362 of spring arms 360 such that the most proximal portion of the mesh sits free within the proximal portion of the mesh stabilizer 30 to prevent the mesh from obscuring the view during suturing of mesh to vagina. The mesh can be threaded over the respective middle tine 362, or over all three tines in a fluctuating manner. The innermost surface of the spring arm tines 362 may be textured, for example with serrations or ribs, to prevent slippage or pop-off of the mesh stabilizer 30 from the vaginal muscularis. This way, each spring arm 360 carries one strap of mesh.

The two opposing spring arms 360 of the stabilizer 30 are semi-flexible/resilient to assist the spreadable spring function, and may be mounted by spring-hinges inside body 320. In addition to the spring arms 360, the mesh stabilizer 30 includes two opposing foldable mesh dispensers 340 for dispensing the remaining portion of the sacral mesh via the spring arms 360. Each dispenser 340 includes a hollow elongate rectangular shroud 341 likewise pivotally mounted to the body and spring-biased outward. In one embodiment, a bobbin or spool (obscured) may be pivotally mounted lengthwise inside each shroud 341, and a roll of sacral mesh is/can be wound about the spool. This way, the wound mesh can be freely dispensed to suit the surgeon's needs through a dispensing slot 342 along one side of the dispenser 340, onto the tines 362 about which the mesh is woven. In another embodiment, the mesh is collapsed inside the shroud 341 in a folded accordion fashion, which then freely feeds out of the shroud 341 as needed by the surgeon.

Figure 9:
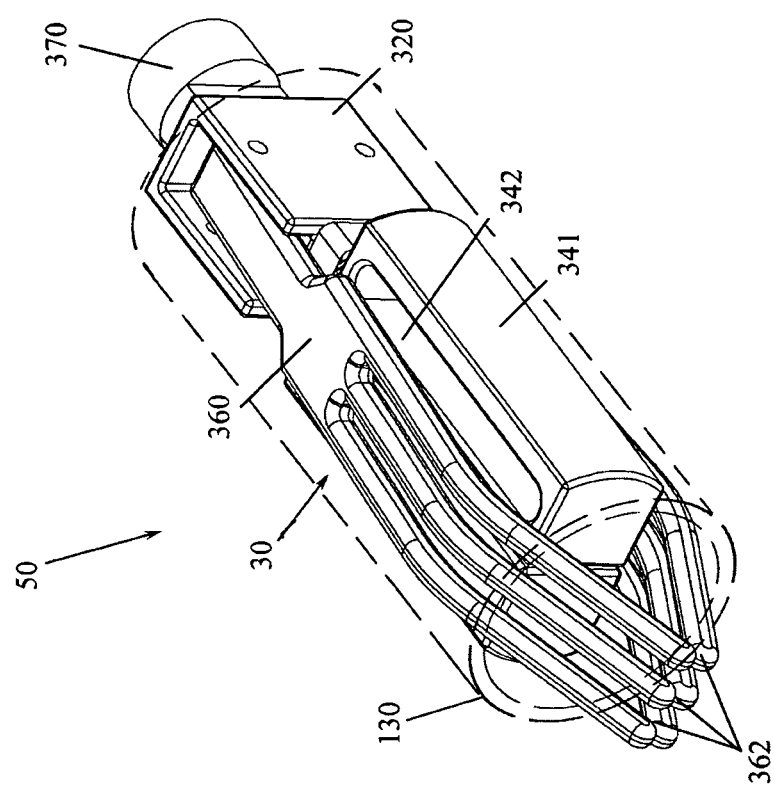
FIG. 9 is a perspective view of the preloaded compact mesh stabilizer 30.

The mesh stabilizer 30 is packaged as a pre-loaded (or semi-preloaded) sub-assembly 50 inside holder tube 130 as shown on FIG. 9. The opposing spring arms 360 and opposing foldable mesh dispensers 340 are folded together (collapsed) with the preloaded mesh strips (that have been pre-woven onto the spring arms 360, with excess mesh loaded inside the dispensers 340). This mesh stabilizer 30 is slidably preloaded into the holder tube 130, and the resulting sub-assembly 50 is then attached to introducer 20 by magnet 370, which facilitates insertion through a trocar into the abdomen. The sub-assembly 50 and introducer 20 are feed into a standard trocar by the surgeon or assistant. As this sub-assembly 50 is pushed down into the trocar 22, the holder tube 130 will not pass through the trocar 22, but instead catches within the trocar 22 to eject the mesh stabilizer 30. The exposed mesh stabilizer 30 and distal end of the introducer 20 continue to be pushed through the trocar 22 and into the abdomen area. Note that the insertion of the holder tube 130 into the trocar 22 may require a removable end-cap on the trocar 22 (not shown) which could be removed for insertion of the sub-assembly 50. Once the mesh stabilizer 30 and distal end of introducer 20 pass through the trocar 22, capturing the holder tube 130 therein, the end-cap can be removed from the holder tube 130 for evacuation of the holder tube 130 there from.

When the mesh stabilizer 30 is deployed into the abdomen area, the opposing spring arms 360 and opposing foldable mesh dispensers 340 unfurl to their open position (shown in FIGS. 4-5). The probe 10 is inserted into a fixed opposing position within the vagina, and the mesh stabilizer 30 slides over and docks with the probe 10, collapsing around the front and back walls of the vaginal cavity. At this point, the mesh stabilizer 30 is fully docked with the probe 10 and they sandwich both the mesh and vaginal muscularis there between so that one strap of mesh sits opposed to the front vaginal wall and a separate strap to the back vaginal wall. This securely positions the mesh on the vaginal walls to which it will be sutured, and adds some frictional resistance to withdrawal of the mesh through the tines 362.

As mentioned above with regard to FIG. 9, the stabilizer 30 is initially contained inside holder tube 130 and permanent magnet or ferromagnetic material 370 engages a small permanent magnet or ferromagnetic material 132 insert at one end of the introducer 20 (see FIG. 3). The mesh stabilizer 30 magnetic or ferromagnetic material insert 370 is secured to the back of the housing 320 to facilitate docking and also selective release of the mesh stabilizer 30 from the introducer 20 and onto the probe 10 once it has been docked. The introducer 20 is simply manually retracted (pulled back) by the surgeon to overcome and break the magnetic attraction, and can then be removed. If a physical grabber is used in place of or in addition to the magnetic inserts 132, 370, the grabber would be released at the manipulator stem 126 via cables or linkages.

In addition to the spring arms 360, the probe 10 and mesh stabilizer 30 are equipped with interlocking docking assemblies for secure attachment. Thus, while in the open position (illustrated in FIGS. 4-8) the mesh stabilizer 30 interfaces in lock and key fashion with the complementary vaginal probe 10 (the vaginal probe 10 serving as the lock and the mesh delivery/mesh stabilizing system 20 serving as the key). One skilled in the art will understand that a variety of known docking mechanism are known in other contexts and may be adapted for present purposes, and thus are considered within the scope and spirit of the docking concept itself according to the present invention. In the illustrated embodiment, the docking assembly comprises an extending male pin 350 in the mesh stabilizer 30 that is inserted into a female receptacle 110 in the probe 10 (described below). Once in front of the probe 10, the arms 360 of the mesh stabilizer 30 embrace the head of the probe 10 and guide insertion of the locking pin 350 into a small hole in the probe 10. With the pin 350 locked in position, the stabilizer 30 may be detached from the introducer 20, and the introducer 20 removed. Pin 350 is formed or machined with a slightly flattened cross-section, and as seen in FIGS. 5 & 6 it is equipped with serrated surface 352 with serrations spaced lengthwise along its flattened edges, as well as a sharp point to penetrate the vaginal wall. The serrated surface 352 provides a releasable interlock with the female receptacle in the probe 10 (to be described). One skilled in the art should understand that this configuration may be reversed, with extending male pin 350 extending from the probe 10 and a female receptacle located in the mesh stabilizer 30 In this case, the extending male pin from the probe 10 would be inserted into the mesh stabilizer 30 and, if desired, the pin 350 could be used to displace the spring arms 360, closing them around the vaginal cavity. Alternatively, the spring arms can simply clamp over the probe 10 and vaginal walls to provide the same lock-and-key coupling effect.

Figure 10:
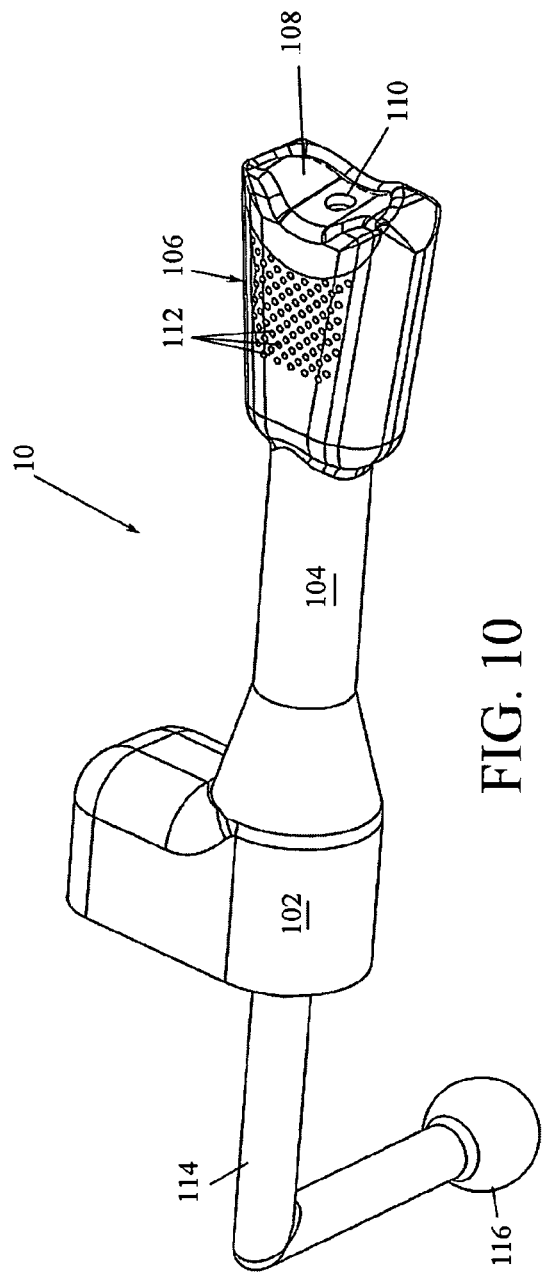
FIGS. 10 and 11 are top and bottom side perspective views, respectively, of the vaginal probe 10.
Figure 11:
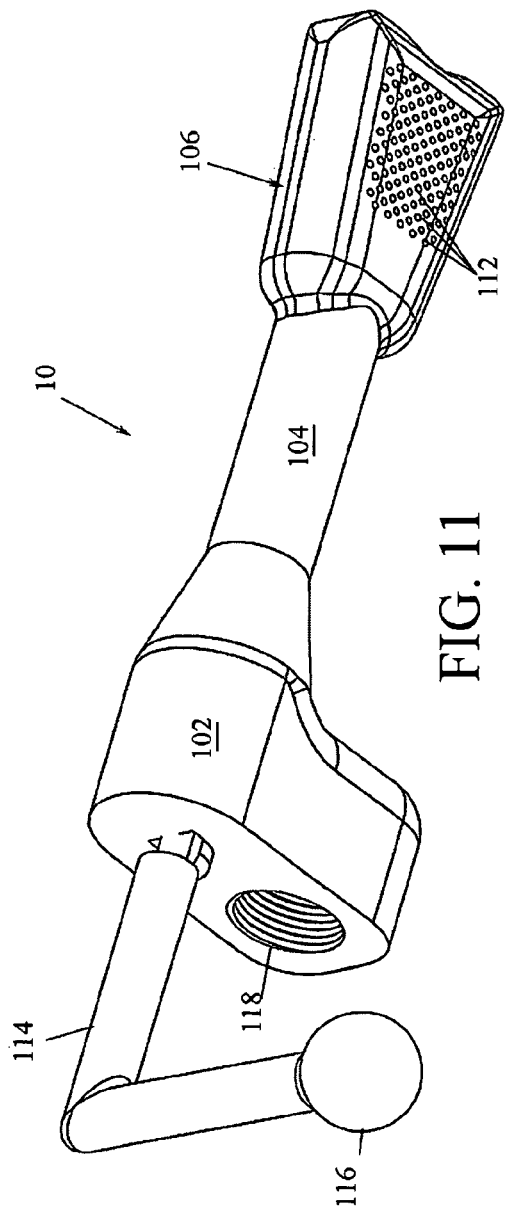

FIGS. 10 and 11 are top and bottom side perspective views, respectively, of the vaginal probe 10. Probe 10 generally comprises a body 102 leading to a shaft 104 for insertion in the vagina, and a probe head 106 distal on the shaft 104. The probe head 106 is flattened, with a generally trapezoidal horizontal and vertical cross-section flaring outward from the shaft 104, with rounded corners and edges. The probe head 106 is larger at the distal tip and has flat anterior and posterior surfaces. The probe head 106 is tapered slightly below the tip to prevent inadvertent pop-off of the mesh stabilizer 30, and this can be achieved with the trapezoidal shape as shown. Exemplary dimensions are 7 cm×5 cm×2.5 cm×4 cm, resulting in a 5 cm×2.5 cm probe end. The thicker tip can help prevent the spring arms 360 of the stabilizer 30 from coming off (if the embodiment relies strictly on clamping).

As shown in FIG. 10, the probe head 106 flares outward to a concave recess within which one of a variety of interchangeable probe tips 108 reside. The concave probe tip(s) 108 are all rearwardly uniform in shape and size, and are forwardly shaped to conform to the curvature of the vaginal apex. However, the concept of interchangeable probe tips 108 is designed to accommodate differently-sized vaginal apices. Patients differ in this regard, and so it is envisioned that an array of interchangeable probe tips 108 will be provided with varying concave radii of curvature to allow the surgeon a selection for best fit during surgery.

The flattened probe head 106 is also defined by a plurality of vacuum apertures 112 spaced across both top and bottom surfaces. The vacuum apertures 112 are all connected to a vacuum passage 113 inside the shaft 104 and leading into the body 102. The vacuum passage 113 opens from the rear of the body through a threaded port 118 to which a vacuum source can be connected. This causes the vacuum apertures 112 to adhere to the surrounding vaginal tissue and essentially act as a stabilizer for the vaginal tissue during a variety of surgical procedures, including dissection of the bladder and rectum away from the vagina and then during suturing of mesh to the vagina.

Figure 12:
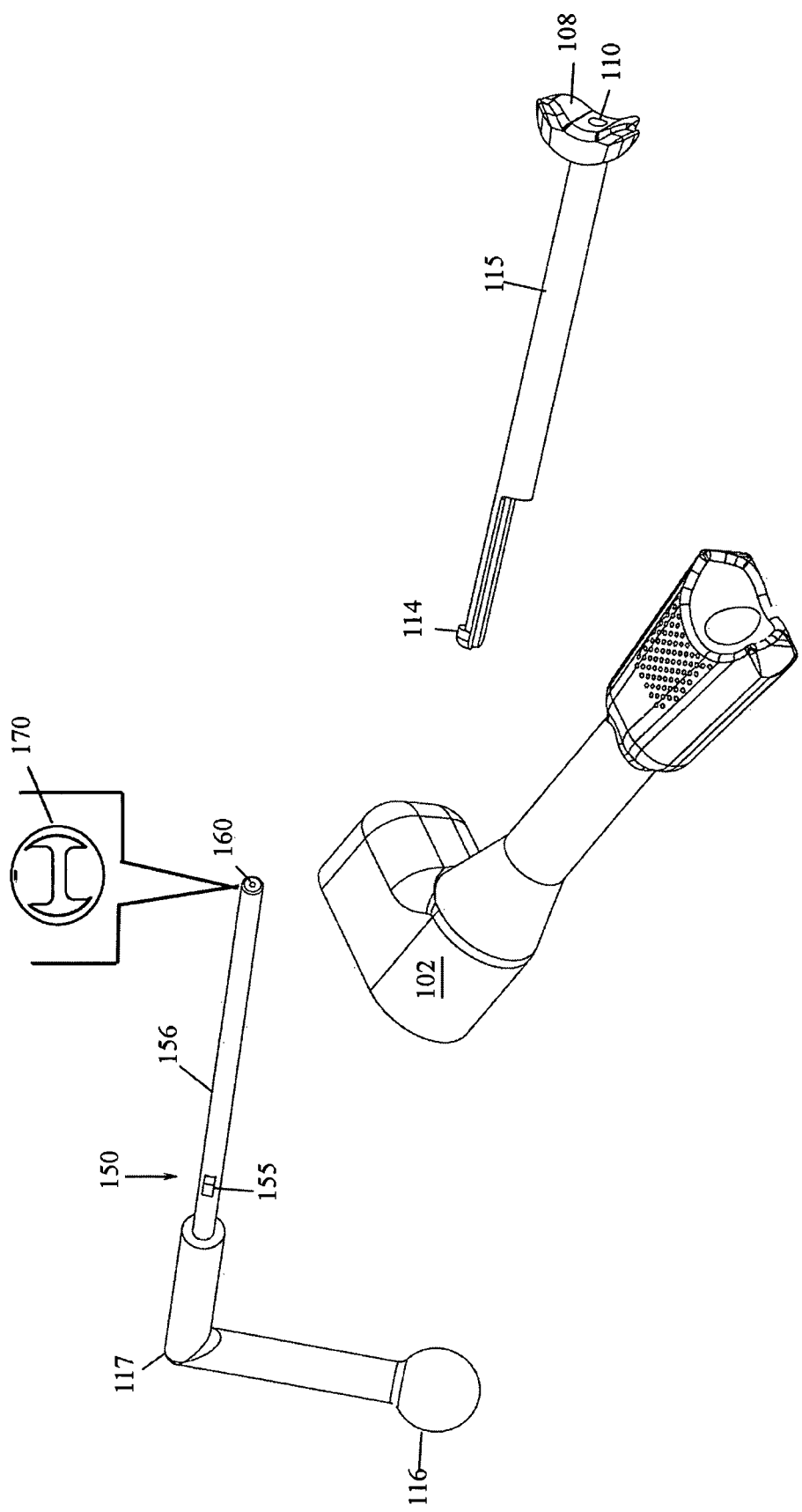
FIG. 12 is an exploded perspective view of the vaginal probe 10 illustrating an example of components of the vaginal probe inclusive of probe body 102, replaceable probe tip 108, and locking lever 150 is inserted into the probe body 102.

FIG. 12 is an exploded perspective view of the vaginal probe 10 illustrating insertion of the probe tip 108. The periphery of the probe tip 108 conforms to the head 106 of probe 10 and seats flush within the distal concavity. The probe tip 108 itself is concave as described above, the curvature of the concave portion varying as necessary to conform to the curvature of the vaginal apex. To facilitate interchangeability, the probe tip 108 is mounted distally on a tubular stem 115 that is inserted lengthwise into a receiving channel running centrally and axially throughout the body 102, shaft 104, and probe head 106 of probe 10. The tubular stem 115 terminates at a locking lip 114 by which the probe tip 108 and stem 115 are retained within the probe 10. A locking lever 150 is inserted rearwardly into the probe body into the receiving channel of stem 115. The locking lever 150 includes a cylindrical shaft 156 that fits lengthwise through the tubular stem 115 of the probe tip 108. The locking lever 150 is manually rotated therein by an angle arm 117 that terminates at a knob 116. Rotation of locking lever 150 turns a protruding tooth 155 on the stem 156 that engages behind the locking lip 114 of probe tip 108. In the illustrated embodiment, the locking lip 114 is an annular 180 degree lip. Thus, the locking lever 150 can be turned from an initial unengaged position in which the protruding tooth 155 does not yet engage the locking lip 114 (allowing the probe tip 108 and stem 115 to be removed), to a second engaged position in which the protruding tooth 155 seats behind the locking lip 114 to prevent removal of the probe tip 108 and stem 115. The cylindrical shaft 156 of locking lever 150 terminates at a face defined by an axial aperture 160. When inserted into the stem 115, the face of the shaft 156 seats within the probe tip 108 with the axial aperture 160 centrally exposed through the aperture 110 of the probe tip 108. A retaining member 170 is seated within the tip of the cylindrical shaft 156 of locking lever 150 (see FIG. 11 enlarged inset). In the illustrated embodiment, the retaining member 170 is a thin ring with central aperture defined by opposing tabs. With the locking lever 150 in its second engaged position, when the extending male pin 350 in the mesh stabilizer 30 is inserted into the axial aperture 160 of the stem 115, the serrated surface 352 of the pin 350 interlocks with the tabs of the retaining member 170 to prevent withdrawal. Conversely, when the locking lever 150 is rotated to its initial unengaged position, the flattened pin 350 orients between the tabs of the retaining member 170, the teeth 352 do not grip, and the pin 350 and mesh stabilizer 30 can be freely removed. This facilitates the selectable docking feature of the mesh stabilizer 30 according to the present invention. With mesh stabilizer 30 docked, the probe head 106 fits inside the opposing arms of the mesh stabilizer 30, and deployment in this manner results in trapping of the vaginal walls between the opposing arms of the stabilizer 30 (and the anterior and posterior mesh straps) and the probe head 106, thereby locking the mesh stabilizer 30 in place. In this locked position it is possible to adjust the positioning of the mesh straps 40 separately in front and back. Note that the ends of the mesh straps are retained within the stabilizer 30 so that they do not obscure the view of the posterior vaginal wall when suturing posteriorly. Once the mesh stabilizer 30 is locked in place with the vaginal probe 10, it is recommended to temporarily detach the mesh stabilizer 30 from the introducer 20 by releasing magnetic couplings between 132 and 370, thereby freeing up the laparoscopic port for use of other instruments or to facilitate anterior and superior movement of the probe 10 during suturing. Once suturing is complete, the introducer 20 may be reinserted and reattached to the mesh stabilizer 30 via recoupling 132 to 370 to facilitate retrieval of the mesh stabilizer 30. The handle of introducer 20 allows proper positioning during reattachment to and subsequent removal of the mesh stabilizer 30.

FIG. 13 is a top cross section of the vaginal probe 10, and FIG. 14 is a side cross section, collectively illustrating the vacuum apertures 112 covering the medial top of the probe head 106. The vacuum apertures 112 are small capillary holes all connected via the vacuum passage 113 to the threaded port 118 which opens to the rear of the body 102 offset to one side away from lever 114. In operation, the vacuum apertures 112 attract and retain the vaginal wall tissue when a negative vacuum is applied to port 118 by an external vacuum source. By applying negative pressure, the vaginal tissue is sucked against the probe head 106, thereby preventing sliding movement of the probe 10. The negative pressure is preferably monitored and kept constant, and this is easily accomplished via pressure gauges supplied with commercial vacuum sources. Stabilizing the probe 10 in this manner facilitates the docking operation of the mesh stabilizer 30 to the probe 10. FIG. 13 also illustrates the retaining member 170 seated immediately in advance of the axial aperture 160 leading into the stem 115.

Thus, the operating sequence of the mesh stabilizer 30 and endoscopic introducer 20 designed for use with the vaginal probe 10 generally includes six discrete steps: 1) introduction; 2) opening; 3) coupling; 4) detachment; and 5) suturing.

At 1) introduction, the mesh stabilizer 30 is loaded inside the holder tube 130 and attached to the distal end of the introducer 20. In this state, the spring arms 360 are constrained in a closed state for endoscopic introduction into the abdomen.

At 2) opening, the introducer 20 (FIG. 3) and mesh stabilizer are loaded into a trocar and pushed through the abdomen, extending into abdomen region. Once in the abdomen region, the stabilizer 30 is exposed (pushed from holder tube 130), and spring arms 360 of the mesh stabilizer 30 open to a parallel (or beyond parallel) position.

At step 3) coupling, the open spring arms 360 are advanced over the probe head 106 to begin the lock and key docking between the mesh stabilizer 30 and the vaginal probe head 106. The mesh stabilizer 30 locks onto the vaginal probe head 106, with the spring arms 360 and mesh strips 40 positioned on the front and back walls of the vagina. The interlocking mechanism between the mesh stabilizer 30 and the probe 10 cause a closing action of the spring arms 360 that traps the mesh between the arms 360 and the vaginal muscularis. The probe head 106 remains stationery inasmuch as it is mounted distally on an adjustable stabilizer (as in FIG. 2) which is in turn attached to a support surface. The vacuum apertures 112 also serve to stabilize the probe head 106. One skilled in the art will understand that the probe 10 of FIG. 2 need not be arm-stabilized as shown, but can be handheld or controlled with the use of a surgical robot. The illustrated stabilizer system preferably provides three-axis adjustment of the probe head 106. Given this configuration, the interlock serves to temporarily trap the mesh in position on the anterior and posterior vaginal walls.

With the locking lever 150 in its second engaged position, the extending male pin 350 in the mesh stabilizer 30 enters the axial aperture 160 of the stem 115 and its serrated surface 352 interlock with the retaining member 170 to prevent withdrawal. As noted, the location of the male pin 350 and axial aperture 160 could be switched between the mesh stabilizer 30 and probe 10.

At 4) detachment, the introducer 20 is removed from the mesh stabilizer 30 by either overcoming the load bias of the magnetic coupling and breaking the magnetic coupling, and/or by remotely disengaging physical grabbers via linkages or cables. This leaves the stabilizer 30 attached to the probe while the introducer 20 is removed.

At 5) suturing, the surgeon has an unobstructed view of the vaginal muscularis and mesh straps, which facilitates the suturing of the mesh straps to the vaginal muscularis.

Upon completion of suturing, the introducer 20 can be reinserted and reattached to the stabilizer 30 to permit removal of the stabilizer 30.

One skilled in the art should readily understand that there may be other mechanical mechanisms to achieve the requisite docking between the probe head 106 and mesh stabilizer 30, and the illustrated mechanisms are exemplary. In all such cases the probe head 106 (the lock) interfaces in lock and key fashion with the mesh stabilizer 30 such that closing of the spring arms 360 results in trapping of the mesh straps and temporary locking in place of the mesh stabilizer 30 (the key).

In addition to the basic functionality described above, the probe 10 may be modified as desired to improve suitability to task. For example, there may be one probe design for use with a flush vaginal vault, and one for use with a retained cervix. The vaginal vault probe may be equipped with a grasping mechanism at its tip to further stabilize the vagina and minimize the risk of inadvertent pop-off of the mesh stabilizer 30. The grasping mechanism may be paired built-in grasping forceps, paired conical tips that prevent slippage without grasping, or paired suction channels to prevent slippage by creating a vacuum between the probe and the vaginal muscularis. A retained cervix vaginal probe must accommodate the cervix at its anterior tip. This may entail a shorter probe component that would sit within the endocervix to stabilize the cervix. Again, the probe 10 may contain some form of grasping component as described above to further stabilize the cervix and pull it flush against the probe.

One skilled in the art will understand that the above-described vaginal probes 10 are also well-suited for use as uterine manipulators. Uterine manipulators are frequently used during laparoscopic gynecologic surgery to allow elevation, deflection, stabilization, and rotation of the uterus. These manipulators typically contain a probe that passes into the endocervical canal, and sometimes beyond to extend into the uterine cavity. The manipulators are typically retained by either an inflatable balloon at the tip of the probe that is inflated once the tip is in the uterine cavity to prevent retraction through the endocervical canal, or by use of a tenaculum placed to grasp the ectocervix on end and stabilizing the endocervical probe on the other end, or by some combination of the two. However, this approach has several limitations. First, it is inefficient in that it requires a surgical assistant to occupy one hand to hold and maneuver the uterine manipulator. This inefficiency is particularly evident during robotic surgery where the robot occupies the space between the patient's legs, rendering holding of the uterine manipulator by the surgical assistant particularly awkward. Second, the ability to deflect and rotate the uterus is inconsistent because of rotation of the probe within the uterine cavity due to the probes round contour. Hysterectomy is increasingly being performed laparoscopically or robotically.

The round contour of the uterine manipulator probes makes them unlikely to alter the contour of the uterine cavity when the uterus is being retained but when hysterectomy is intended, preservation of the contour of the uterine cavity is no longer a concern. Therefore, the ideal probe for hysterectomy may have different attributes than the uterine manipulator used during uterine sparing surgery. One such embodiment would be configured in an expandable fan shape that conforms to the natural contour of the uterine cavity, thereby preventing spinning of the manipulator within the cavity rendering it more effective for precise uterine positioning.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

INDUSTRIAL APPLICABILITY

A common remedial surgical procedure for the correction of pelvic organ prolapse, and the standard procedure for correction of prolapse of the upper vagina, is sacral colpopexy. In the latter cae, the sacral colpopexy operation recreates support to the upper vagina by attaching straps of permanent synthetic mesh to the upper anterior and posterior vaginal walls and then suspending the other end of the straps on the anterior surface of the sacrum. The sacral colpopexy operation is usually performed through a large incision in the abdominal wall (laparotomy). However, there is growing interest in performing this operation via less invasive approaches, such as laparoscopy or robot-assisted laparoscopic surgery. Unfortunately, existing vaginal probes, surgical instruments and mesh configurations are not well-suited for this. Sacral colpopexy has been attempted laparoscopically through multiple ports, in one case three to four ports for access by a daVinci® robot, and one or two ports for an assistant. Nevertheless, whether performed manually or robotically, there remain inherent problems with manipulating the end effectors, positioning of the mesh straps, and stabilizing the vagina. Specifically, guiding the mesh straps into proper orientation is awkward, and maintaining them in the proper position during suturing requires constant vigilance on the part of the assistant especially since they frequently require repositioning. The effort occupies one or more instruments that could be utilized elsewhere, and the instruments or the mesh often obscure the site of interest, particularly during suturing the posterior strap of mesh to the posterior vaginal wall. Consequently, there would be great industrial applicability for a mesh delivery system that overcomes the alignment and positioning problems using a docking concept as above, rendering the mesh attachment for sacral colpopexy more efficient. By simplifying the operation it becomes less time consuming, less prone to error, lowers the learning curve, and increases the potential for the operation to be completed laparoscopically.

What is claimed is:

1. A mesh delivery system for use in performing sacral colpopexy on a female patient, comprising:
   an elongate introducer for insertion through an abdominal wall of said female patient;
   a mesh stabilizer detachably connected to said introducer, said mesh stabilizer including a pair of arms for holding and positioning mesh straps on an exterior wall of said female patient's vagina, and a first docking member;
   a vaginal probe for insertion into said female patient's vagina, said vaginal probe having a probe head for positioning against an interior wall of said female patient's vagina, and a second docking member integral to said probe head for coupling to the first docking member of said mesh stabilizer;
   whereby said introducer carries and delivers the mesh stabilizer into said female patient's abdominal area through a first incision, said vaginal probe is inserted into said female patient's vagina, and said mesh stabilizer is coupled by said first docking member to the second docking member on the probe head of said vaginal probe to stabilize said mesh straps against said female patient's vaginal apex for suturing.

2. The mesh delivery system according to claim 1, wherein the introducer is adapted to be selectively detached from the mesh stabilizer and removed from the abdomen to facilitate suturing of the mesh to the anterior and posterior vaginal walls.

3. The mesh delivery system according to claim 2, wherein after suturing of mesh to the vagina is complete, the introducer is adapted to be reinserted into the abdomen and reattached to said mesh stabilizer for retrieval of the mesh stabilizer.

4. The mesh delivery system according to claim 1, wherein said mesh stabilizer comprises a resilient spring arm for supporting and carrying a strip of sacral mesh.

5. The mesh delivery system according to claim 4, wherein said mesh stabilizer comprises two opposing resilient spring arms for supporting and carrying two strips of sacral mesh.

6. The mesh delivery system according to claim 1, wherein said introducer comprises a distal attachment mechanism with selective release for selectively releasing said mesh stabilizer.

7. The mesh delivery system according to claim 6, wherein said attachment mechanism comprises a magnet.

8. The mesh delivery system according to claim 1, wherein said introducer comprises at least one articulated joint for exterior manipulation of said mesh stabilizer when inside said body cavity.

9. The mesh delivery system according to claim 8, wherein said introducer comprises three segments pivotally joined endwise at two articulated joints, and movement of one end-segment moves the other end-segment.

10. The mesh delivery system according to claim 1, wherein said probe comprises a vacuum port for attachment of an external vacuum source, and said vacuum port is in communication with a plurality of vacuum apertures in said probe head.

11. A sacral mesh delivery system, comprising:
    a mesh stabilizer for securing and positioning sacral mesh, said mesh stabilizer having a first docking member;
    a vaginal probe for insertion into said female patient's vagina, said vaginal probe having a probe head and a second docking member integral to said probe head for releasable coupling to the first docking member of said mesh stabilizer; and
    an introducer for inserting said mesh stabilizer into a body cavity and docking said mesh stabilizer by said first docking member to the second docking member on the probe lead of said probe for anchoring said sacral mesh thereto during suturing.

12. The sacral mesh delivery system according to claim 11, wherein said mesh stabilizer comprises at least one resilient spring arm for supporting and carrying a strip of sacral mesh.

13. The sacral mesh delivery system according to claim 12, wherein said introducer comprises a distal attachment mechanism with release control for attaching and selectively releasing said mesh stabilizer.

14. The sacral mesh delivery system according to claim 13, wherein said attachment mechanism comprises a magnet.

15. The sacral mesh delivery system according to claim 12, wherein said introducer comprises at least one articulated joint for exterior manipulation of said mesh stabilizer when inside said body cavity.

16. The sacral mesh delivery system according to claim 15, wherein said introducer comprises three segments pivotally joined endwise at two articulated joints, and movement of one end-segment moves the other end-segment.

17. The mesh delivery system according to claim 12, wherein said probe comprises a vacuum port for attachment of an external vacuum source, and said vacuum port is in communication with a plurality of vacuum apertures in said probe head.

* * * * *